(12) United States Patent
Huang

(10) Patent No.: US 11,918,947 B2
(45) Date of Patent: Mar. 5, 2024

(54) ISOLATION WARD STRUCTURE

(71) Applicant: VERO VERIA CORPORATION, New Taipei (TW)

(72) Inventor: Chien Teh Huang, New Taipei (TW)

(73) Assignee: VERO VERIA CORPORATION, New Taipei (TW)

( * ) Notice: Subject to any disclaimer, the term of this patent is extended or adjusted under 35 U.S.C. 154(b) by 784 days.

(21) Appl. No.: 17/031,911

(22) Filed: Sep. 25, 2020

(65) Prior Publication Data
US 2022/0023787 A1    Jan. 27, 2022

(30) Foreign Application Priority Data

Jul. 24, 2020 (CN) .......................... 202010722493.5

(51) Int. Cl.
*G09F 7/18*      (2006.01)
*A61L 9/20*      (2006.01)
(Continued)

(52) U.S. Cl.
CPC .......... *B01D 46/0028* (2013.01); *A61L 9/205* (2013.01); *B01D 46/0041* (2013.01);
(Continued)

(58) Field of Classification Search
CPC .... F24F 8/10; B01D 2279/65; B01D 2279/51
See application file for complete search history.

(56) References Cited

U.S. PATENT DOCUMENTS 2,997,132 A * 8/1961 Dock ...................... B08B 15/00
                                                   454/365
3,356,006 A * 12/1967 Scott ..................... B01D 46/523
                                                    55/470
(Continued)

FOREIGN PATENT DOCUMENTS

TW          I233365          6/2005
TW          I248810          2/2006
(Continued)

*Primary Examiner* — Basil S Katcheves
(74) *Attorney, Agent, or Firm* — Best & Flanagan LLP

(57) ABSTRACT

An improved isolation ward structure includes a top portion further comprising a space, a fresh-air pipe, a communication pipe and a an exhaust-connected pipe wherein the space is furnished with an air filtration unit (FFU); an end of the communication pipe is communicated with the fresh-air pipe while its other end is communicated with the air filtration unit (FFU), an end of the exhaust-connected pipe is communicated with the fresh-air pipe; a bedroom being positioned under the air filtration unit (FFU) will let the air which is filtered through the air filtration unit (FFU) enter the bedroom; a bottom portion being positioned under the bedroom has a semi-hermetic space formed by the plurality of elevated honeycomb floors; the air within the bedroom will enter the semi-hermetic space which will let the pathogenic air within the bedroom (10) flow therein via the plurality of honeycomb floors (22) and re-circulate through the air filtration unit (FFU) to be filtered; and a backflow circulation portion being positioned above the semi-hermetic space and below the space with its upper end communicates with the other end of the exhaust-connected pipe; the backflow circulation portion is adjacent to the bedroom for re-circulating the air waited to be filtered within the semi-hermetic space to the fresh-air pipe therein.

21 Claims, 10 Drawing Sheets

(51) Int. Cl.
   *B01D 46/00*   (2022.01)
   *F24F 8/10*   (2021.01)
   *F24F 11/00*   (2018.01)
   *E04H 3/08*   (2006.01)
   *F24F 110/50*   (2018.01)

(52) U.S. Cl.
   CPC ............ *F24F 8/10* (2021.01); *F24F 11/0001* (2013.01); *A61L 2202/25* (2013.01); *B01D 2279/51* (2013.01); *B01D 2279/65* (2013.01); *E04H 3/08* (2013.01); *F24F 2011/0002* (2013.01); *F24F 2110/50* (2018.01)

(56) References Cited

U.S. PATENT DOCUMENTS

| | | | | |
|---|---|---|---|---|
| 4,600,419 | A | * | 7/1986 | Mattison .............. B01D 46/521 55/508 |
| 4,883,511 | A | * | 11/1989 | Gustin ................... F24F 3/167 55/385.2 |
| 5,643,081 | A | * | 7/1997 | Klein ....................... F24F 8/10 55/506 |
| 5,871,556 | A | * | 2/1999 | Jeanseau ................ B01D 46/10 55/385.2 |
| 5,993,311 | A | * | 11/1999 | Feller ..................... E04B 9/064 55/355 |
| 2003/0089231 | A1 | * | 5/2003 | Fujii ..................... B01D 53/26 95/117 |
| 2005/0039600 | A1 | * | 2/2005 | Lim ...................... B01D 46/58 55/471 |
| 2005/0160706 | A1 | * | 7/2005 | Kim .......................... F24F 8/10 55/385.2 |
| 2005/0268585 | A1 | * | 12/2005 | Morse ..................... F24F 13/28 55/502 |
| 2006/0174596 | A1 | * | 8/2006 | Choi ..................... F24F 12/006 55/467 |
| 2006/0217056 | A1 | * | 9/2006 | Gomi ..................... F24F 8/108 55/385.2 |
| 2010/0105309 | A1 | * | 4/2010 | Ishibashi ................ F24F 8/108 454/49 |
| 2012/0285459 | A1 | * | 11/2012 | Sata ......................... F24F 8/80 128/205.27 |
| 2018/0163978 | A1 | * | 6/2018 | Ziegler ................ A61G 12/004 |
| 2020/0338487 | A1 | * | 10/2020 | Chuang ................. B01D 46/10 |

FOREIGN PATENT DOCUMENTS

| | | |
|---|---|---|
| TW | 201002920 A | 1/2010 |
| TW | M596259 U | 6/2020 |

* cited by examiner

ISOLATION WARD STRUCTURE

BACKGROUND OF THE INVENTION

1. Field of the Invention

An improved isolation ward structure, and more particularly to an improved isolation ward structure capable of performing the treatment of separating the clean air and the pathogenic air by having to input the fresh air and the filtered air through an inlet while having to output the pathogenic air through an outlet.

2. Description of the Prior Art

The treatment of traditional isolation ward performs filtration within the hermetic space. Although filtration is performed, most of the air after being filtered is recycled to utilize again, thereby, it is unable to rapidly, effectively and intrinsically lower the quantity of virus in the air. Thereby, all the patients stay within this space are apt to be infected. Sometimes, if there are numerous of infected patients, the quantity of virus in the air keeps increasing instead of diminishing.

In view of the infection status of the new crown virus in the crowds such as ships, hospitals, etc., traditional isolation wards obviously cannot cope with such a ferocious virus. Therefore, how to design a new negative pressure ward structure that can rapidly and effectively reduce the quantity of pathogenic air without secondary or cluster infections in a hermetic space of the air circulation system will be the active research subject for those familiar in the art.

SUMMARY OF THE INVENTION

The main object of the improved isolation ward structure of the invention is, instead of letting the pathogenic air stay all the time in the negative pressure ward causing the air that needed to be filtered unable to be discharged effectively, to provide a new ward structure that enable the pathogenic air to be discharged through a designated path.

Another object of the improved isolation ward structure of the invention is to rapidly dilute the quantity of virus in the air lest the patients be not easy to gain health recovery.

Preferably, the invention of an improved isolation ward structure includes: a top portion, a plurality of ceilings, a plurality of supporting structures for supporting the plurality of ceilings, wherein the top portion has a space and a clearance room. The space further includes a air filtration unit (FFU) and a fresh-air pipe. The air filtration unit (FFU) is furnished on the plurality of ceilings. The fresh-air pipe is positioned adjacent to the air filtration unit (FFU). the space and the clearance room are arranged in the direction extended along the fresh-air pipe. A bottom portion having a floor, a plurality of floor support structures and a plurality of honeycomb floors in which the plurality of honeycomb floors are installed on the plurality of floor support structures to make the plurality of honeycomb floors become elevated floors above the floor. The floor, the plurality of floor support structures and the plurality of honeycomb floors are arranged in the direction extended along the fresh-air pipe; a first side wall being connected to the top portion and the bottom portion respectively further including an inlet and a fresh air mouth; the fresh air will flow through the fresh air mouth and enter the fresh-air pipe; a second side wall connected to the top portion and the bottom portion respectively; a first adjacent connecting side is formed by connecting the first side wall and the second side wall; a third side wall being connected to the top portion and the bottom portion respectively further including an outlet and an exhaust device; a second adjacent connecting side is formed by connecting the second side wall and the third side wall; a fourth side wall connected to the top portion and the bottom portion respectively; a third adjacent connecting side is formed by connecting the third side wall and the fourth side wall while a fourth adjacent connecting side is formed by connecting the fourth side wall and the first side wall; in this way, a hexagon is then formed; an entrance room, an wind shower room and a circulation room enclosed by the outer surface of the plurality of ceilings, the inner surface of the fourth side wall, the inner surface the first side wall, the inner surface of the second side wall and the outer surface of the plurality of ceilings so as to form by arranging from the first adjacent connecting side along the first side wall toward the first adjacent connecting side, the plurality of ceilings is furnished with the air filtration unit (FFU); a bedroom is formed by the plurality of ceilings and the plurality of honeycomb floors; the bedroom, the entrance room, the wind shower room are separated from one another by a first partition board, there is a communication mouth communicates between the bedroom and the circulation room; a bathroom is formed by enclosing the outer surface of the clearance room, the fourth side wall, the third side wall, the second side wall and the floor.; the bathroom (and the bedroom are separated by a second partition board; the bathroom is communicated with the bedroom through a second communication opening.

Preferably, the air filtration unit (FFU) employs a kind of filter with high efficiency to produce High Efficiency Particulate Air (HEPA).

Preferably, the fresh-air pipe is connected to a fresh air unit of a hospital.

Preferably, the plurality of ceiling boards including the bedroom honeycomb floor positioned in both the bedroom and the circulation room have plurality of perforations to facilitate the passage of air.

Preferably, the first side wall, the second side wall, the third side wall and the fourth side wall employ cement material with Epoxy coated after curing.

Preferably, the first side wall, the second side wall, the third side wall and the fourth side wall are made of brick work.

Preferably, both of the first partition board and the second partition board are storage board with inclined honeycomb trough.

In order to make the aforesaid characteristics and merits more obvious and easier to be understood, the following preferred embodiments and the coordinated brief description of the drawings are described.

BRIEF DESCRIPTION OF THE DRAWINGS

The accomplishment of this and other objects of the invention will become apparent from the following description and its accompanying drawings of which.

DETAILED DESCRIPTION OF THE PREFERRED EMBODIMENT

The invention can be better understood with reference to the detailed content set forth herein and the description of the drawings. Various embodiments will be discussed below with reference to the drawings. However, those skilled in the art will easily understand that the detailed description given here with respect to the drawings is only for the purpose of explanation, because these methods and systems may go beyond the described embodiments. For example, the given teachings and the requirements of specific applications may produce a variety of alternative and suitable methods to achieve any detailed functions described herein. Therefore, any method can extend beyond the specific embodiment options described and illustrated in the following embodiments.

Figure 1:
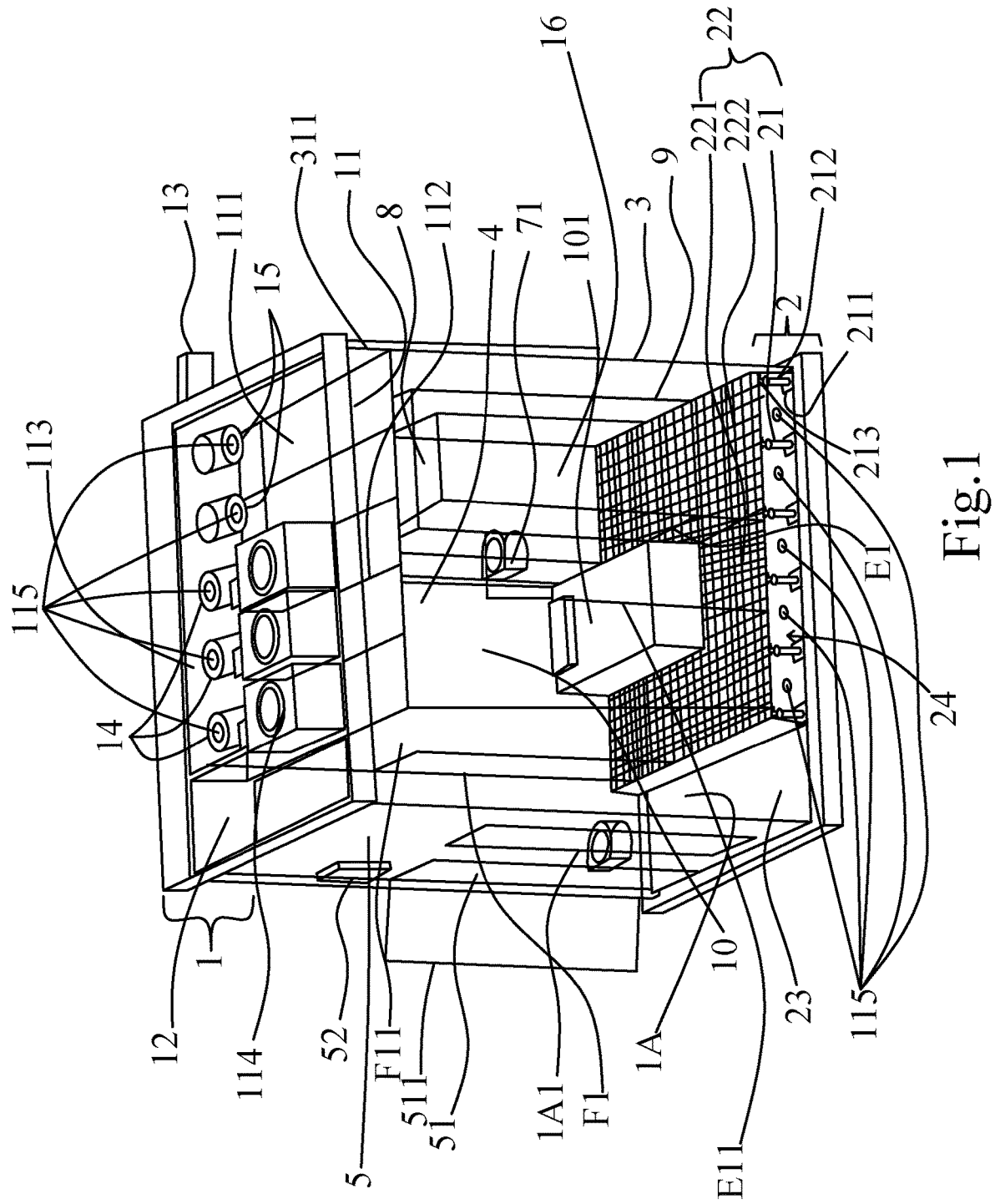
FIG. 1 is an isometric perspective view of a preferred embodiment of an improved isolation ward structure of the invention.

FIG. 1 is an isometric perspective view of a preferred embodiment of an improved isolation ward structure of the invention; while FIG. 2 thru FIG. 7 are a front, a right-hand-side, a left-hand-side, a top, a bottom, and a back perspective views respectively, of the preferred embodiment of the improved isolation ward structure of the invention. As shown in FIG. 1 thru FIG. 7, the improved isolation ward structure includes a top portion (1), a fresh-wind pipe (113), a communication pipe (14) and an exhaust-connected pipe (15). The top portion (1) has a space (11) with an air filtration unit (114) furnished therein. In this embodiment, the air filtration unit (FFU) (114) which employs a kind of high efficiency filter to produce High Efficiency Particulate Air (HEPA) is a Fan Filter Unit. The fresh wind pipe (113) is connected to a fresh air system of a hospital to allow fresh air to enter the air filtration unit (FFU) (114) at any time via a wind pipe (13). The air filtration unit (FFU) (114) is furnished on the plurality of ceilings (111) which are supported by plurality of supporting structures (112). The fresh wind pipe (113) enters the air filtration unit (FFU) (114) through the communicating pipe (14). An inlet of the communicating pipe (14) is connected to the fresh wind pipe (113) and an outlet of the communicating pipe (14) is connected to the air filtration unit (FFU) (114). The fresh wind pipe (113) is positioned above the back portion of the air filtration unit (FFU) (114) to increase the space so as to enhance the filtration effect of the isolation ward.

As shown in FIG. 1, a bedroom (10) is positioned below the air filtration unit (FFU) (114), and the air filtered by the air filtration unit (FFU) (114) enters the bedroom (10).

Figure 10:
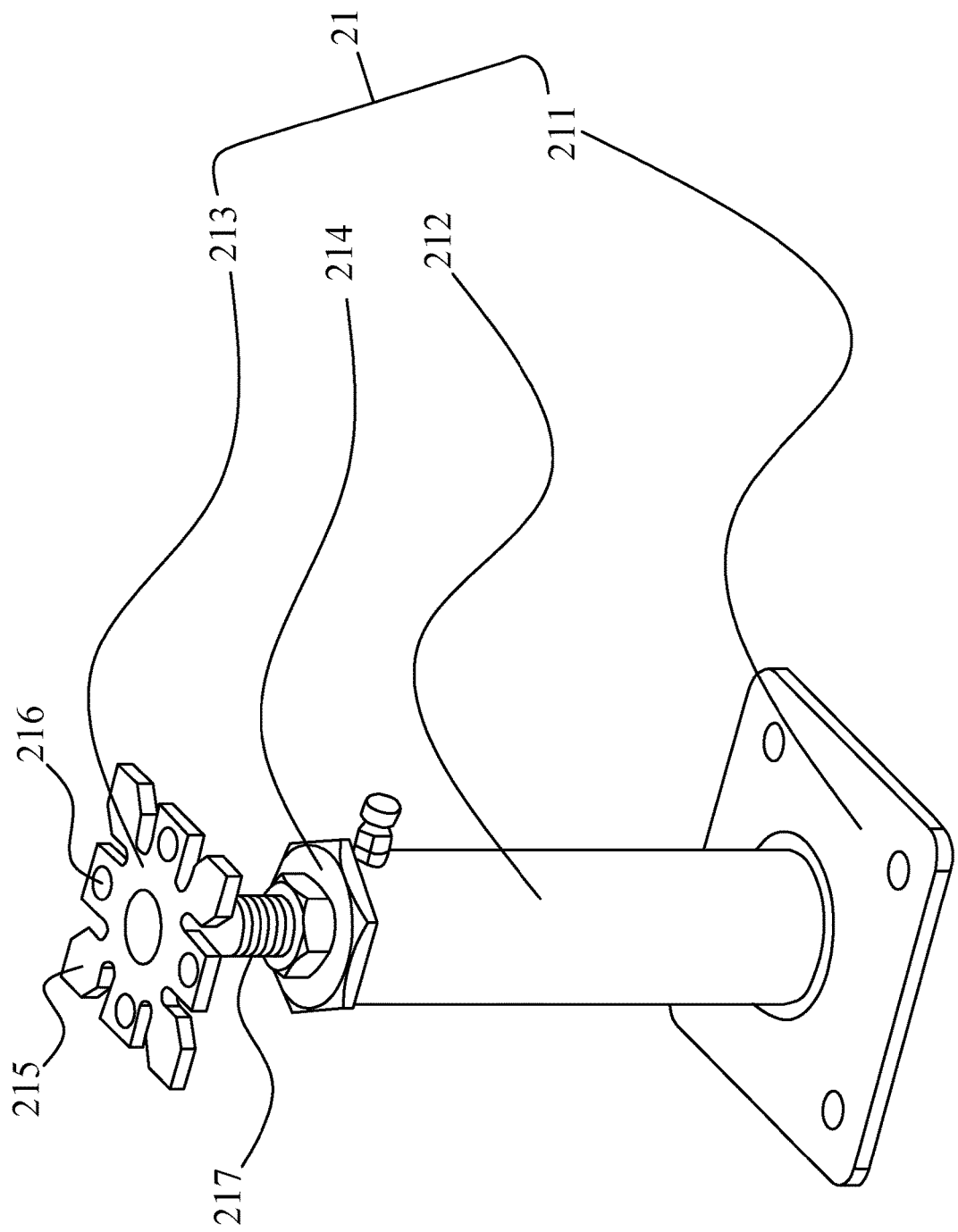
FIG. 10 is a perspective view of a floor supporting structure of the preferred embodiment of the improved isolation ward structure of the invention.

A bottom portion (2) includes a floor (23), a plurality of floor support structures (21), and a plurality of honeycomb floors (22) wherein the plurality of honeycomb floors (22) possess perforations to facilitate the air passage through them during the air circulation and to enhance the air circulation effect. The plurality of floor support structures (21) and the plurality of honeycomb floors (22) are furnished on the floor (23). FIG. 10 is a perspective view of a floor supporting structure of the preferred embodiment of the improved isolation ward structure of the invention. As shown in FIG. 10, the floor support structure (21) further includes a securing seat (211), a supporting tube (212), a tube cover (214) and a supporting seat (213). The plurality of securing seats (211) of the plurality of floor supporting structures (21) are secured on the floor (23). The plurality of honeycomb floors (22) are then mounted on the supporting seat (213). In this way, the plurality of honeycomb floors (22), having the plurality of floor support structures (21) with its supporting tube (212) and their securing seat (211) at their bottom ends as well as their supporting seat (213) at their top ends, form an elevated floor above the floor (23). Moreover, four vertical partitioning planks are furnished to surround the floor (23) and the elevated floor to form a semi-hermetic space (24) making the pathogenic air pass through the honeycomb floors (22) and flow into the semi-hermetic space (24), thereby, circulate again to the air filtration unit (FFU) (114) for filtration.

FIG. 10 is a perspective view of a floor supporting structure of the preferred embodiment of the improved isolation ward structure of the invention. As shown again in FIG. 10, the securing seat (211) and the supporting tube (212) are combined together in which the supporting tube (212) is a hollow body. A tube cover (214) being furnished at its upper end has internal threads. The supporting seat (213) is a T-shaped structure with a top base (215) at its upper end that can be secured to the honeycomb floors (22) through a number of holes (216) by employing screws and nuts. The lower end of the holes (216) is a screw bolt (217) so that the supporting seat (213) can be connected by screwing with the cap on the support tube 212 and can be used to adjust the height of the honeycomb floors (22).

The upper end of a backflow circulation portion (16) being connected to the other end of the exhaust-connected pipe (15) is positioned above the semi-hermetic space (24), below the space (11) and is adjacent to the bedroom (10). Its main function is to make the air to be filtered in the semi-hermetic space (24) flow back and circulates into the fresh air pipe (113) through the exhaust-connected pipe (15).

Figure 2:
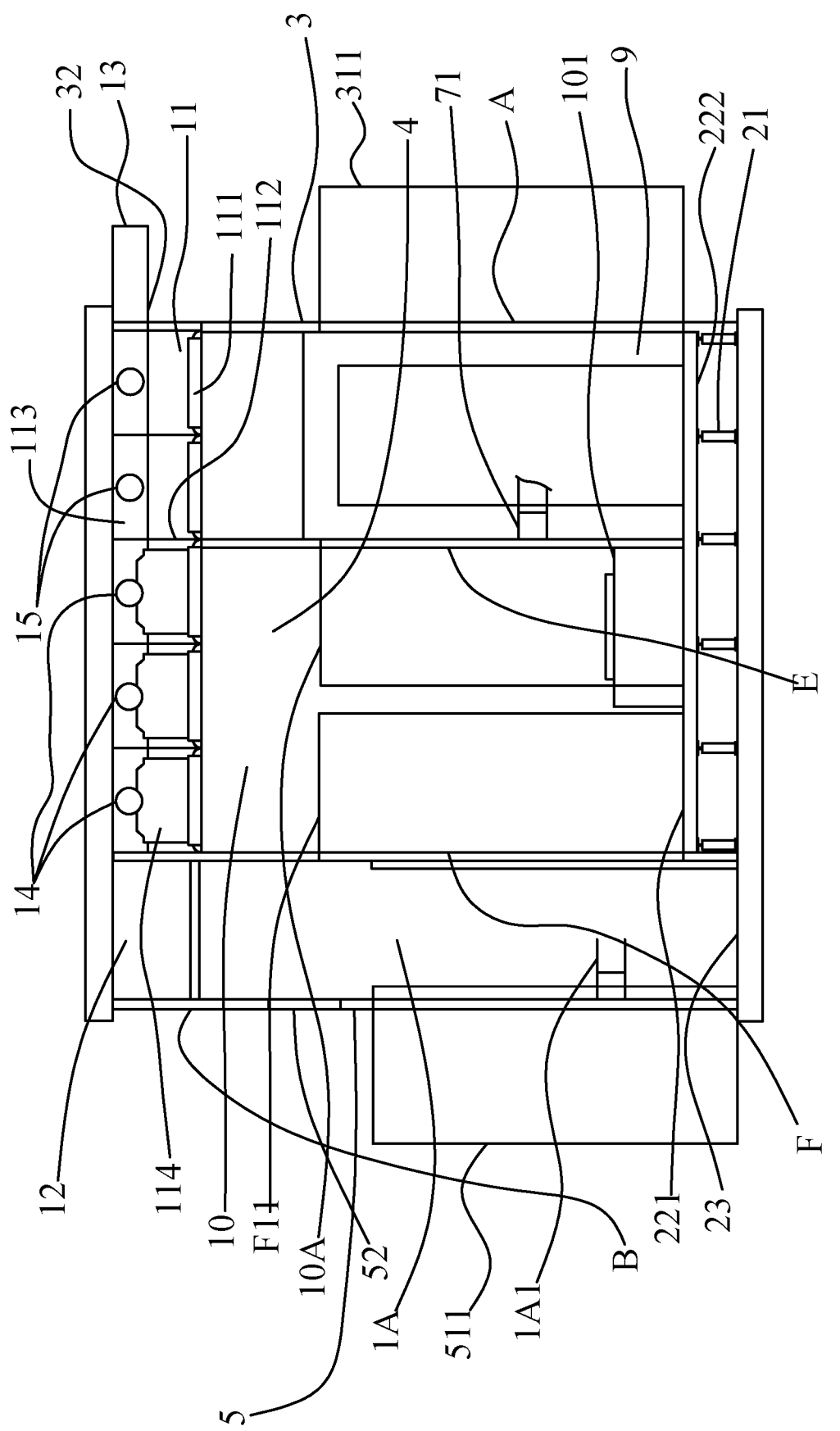
FIG. 2 is a front perspective view of the preferred embodiment of the improved isolation ward structure of the invention.
Figure 3:
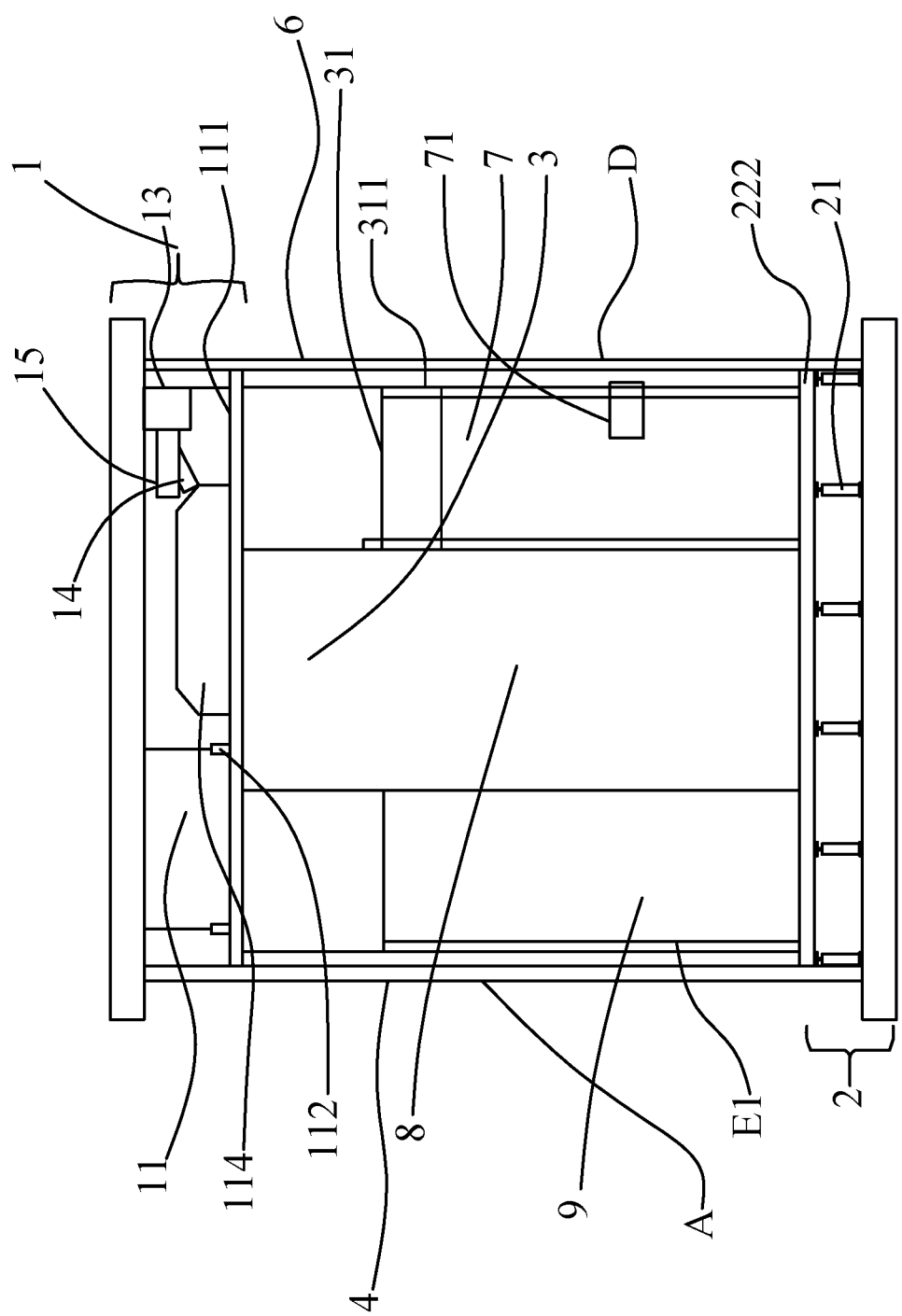
FIG. 3 is a right-side perspective view of the preferred embodiment of the improved isolation ward structure of the invention.

Moreover, a first side wall (3), being connected to the top portion (1) and the bottom portion (2) respectively, possess an inlet (31) (as shown in FIG. 3) and a fresh air mouth (32) (as shown in FIG. 2). The inlet (31) is furnished with an inlet door (311). As shown above, the fresh air in the fresh air system of the hospital will pass through the fresh air mouth (32) and enter the fresh air pipe (113). As shown again in FIG. 1, the first side wall (3) can be brickwork. It can also be made of cement and then coated with epoxy after curing. This epoxy-coated cement, after the epoxy resin is applied, shows electric conductive without being stuck with dust.

Figure 4:
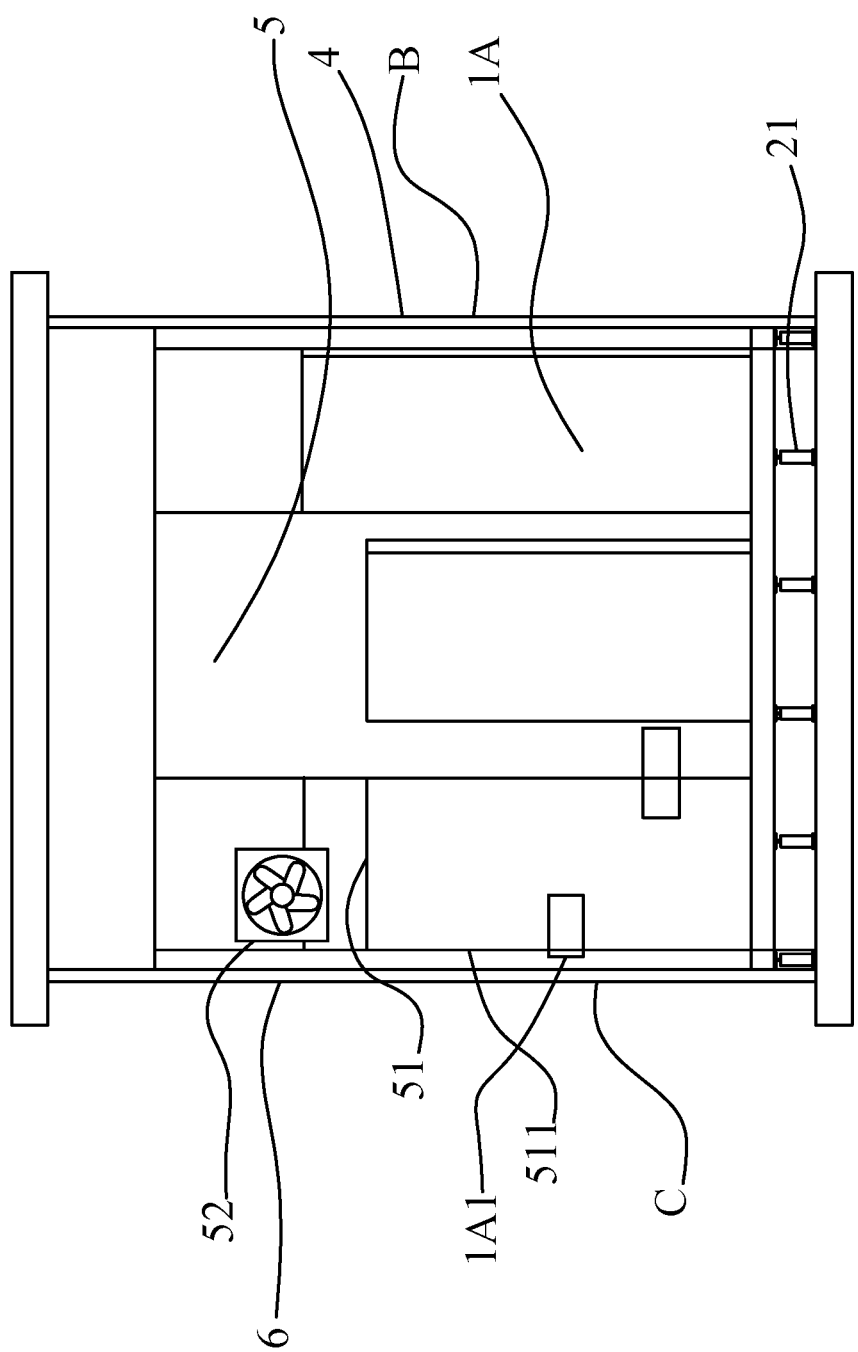
FIG. 4 is a left-side perspective view of the preferred embodiment of the improved isolation ward structure of the invention.
Figure 5:
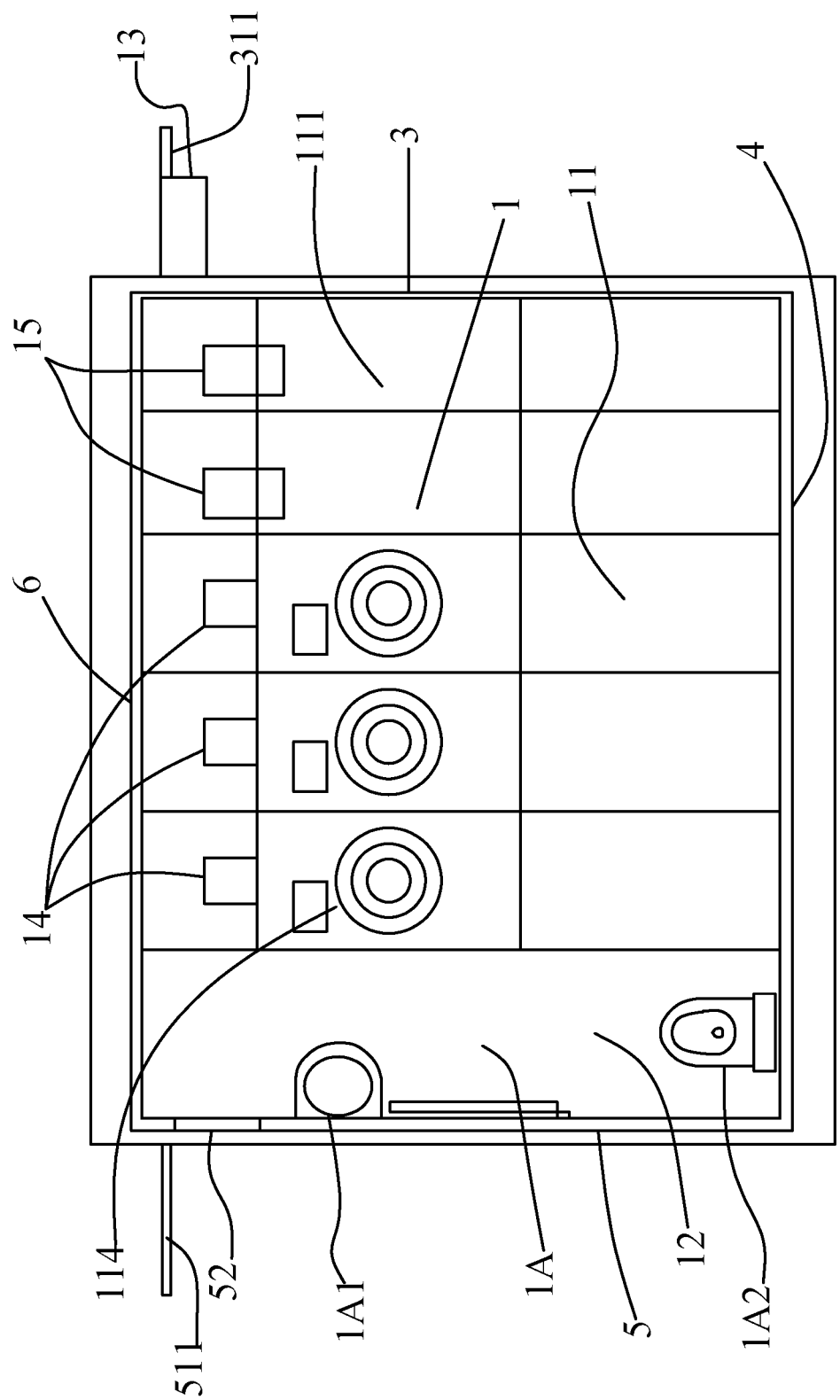
FIG. 5 is a top perspective view of the preferred embodiment of the improved isolation ward structure of the invention.
Figure 6:
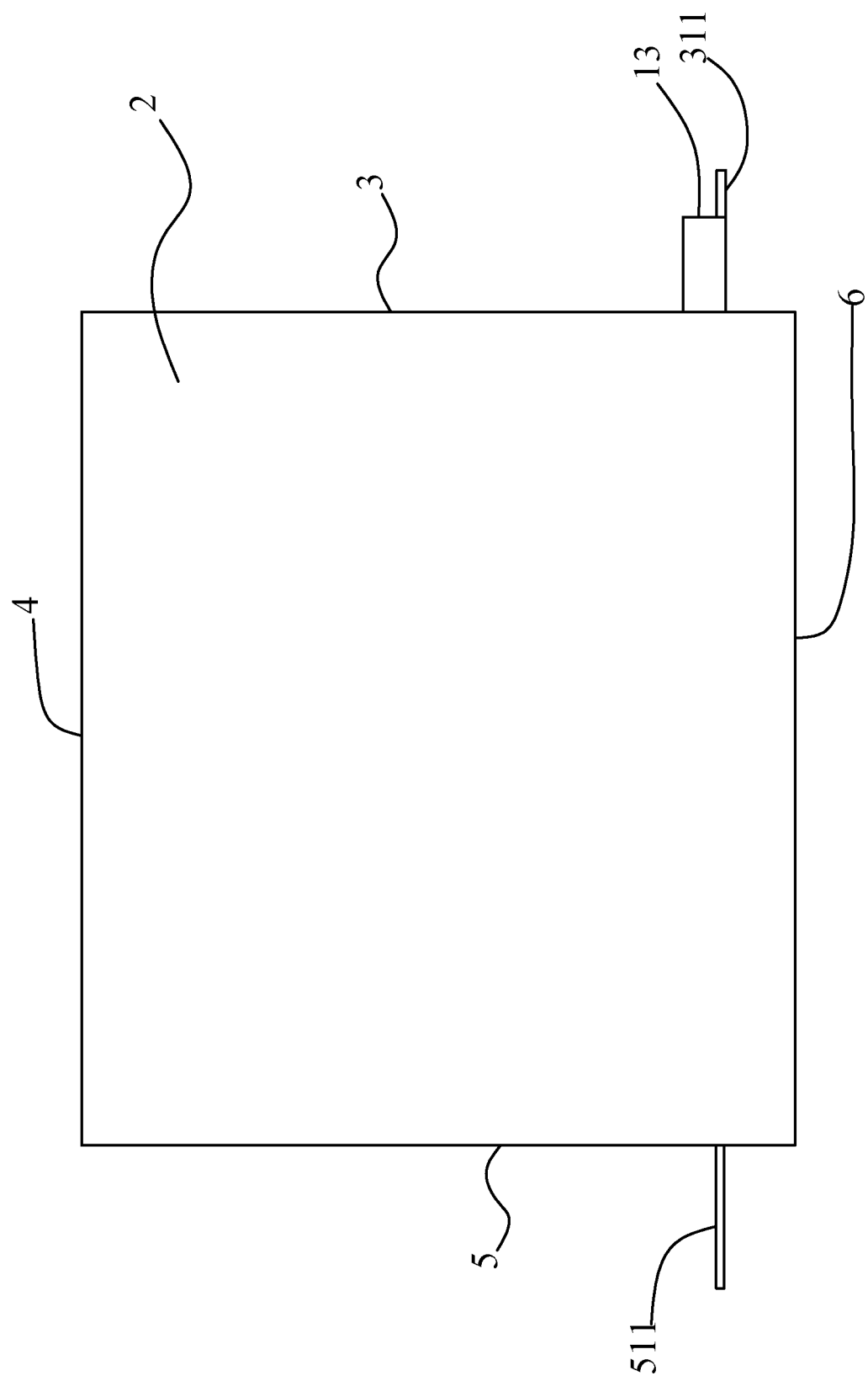
FIG. 6 is a bottom perspective view of the preferred embodiment of the improved isolation ward structure of the invention.
Figure 7:
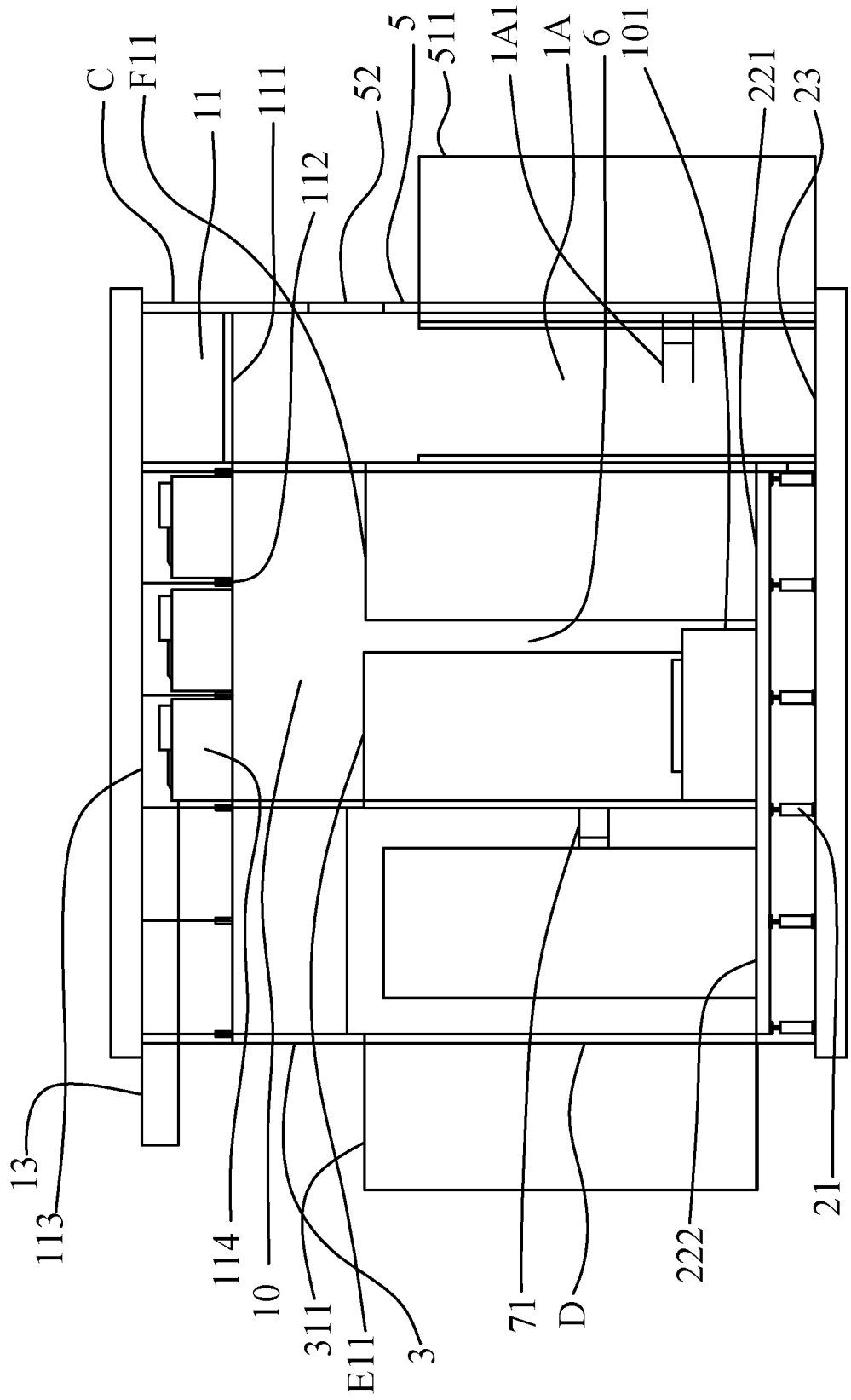
FIG. 7 is a back perspective view of the preferred embodiment of the improved isolation ward structure of the invention.

As shown in FIG. 2, a second side wall (4) is connected to the top portion (1) and the bottom portion (2) respectively. Moreover, the first side wall (3) and the second side wall (4) has a first adjacent connecting side A. The second side wall (4) can be brickwork. It can also be made of cement and then coated with epoxy after curing. This epoxy-coated cement, after the epoxy resin is applied, shows electric conductive without being stuck with dust As shown in FIG. 4, a third side wall (5) is connected to the top portion (1) and the bottom portion (2) respectively. Moreover, the second side wall (4) and the third side wall (5) has a second adjacent connecting side B, an outlet (51) and an exhaust device (52), The outlet (51) is equipped with an outlet door (511) The third side wall (5) can be brickwork. It can also be made of cement and then coated with epoxy after curing. This epoxy-coated cement, after the epoxy resin is applied, shows electric conductive without being stuck with dust As shown in FIG. 7, a fourth side wall (6) is connected to the top portion (1) and the bottom portion (2) respectively. Moreover, the third side wall (5) and the fourth side wall (6) has a third adjacent connecting side (C) while the fourth side wall (6) and the first side wall (3) has a fourth adjacent connecting side (D) In this way, The whole improved isolation ward structure forms a hexahedron. The fourth side wall (6) can be brickwork. It can also be made of cement and then coated with epoxy after curing. This epoxy-coated cement, after the epoxy resin is applied, shows electric conductive without being stuck with dust As shown again in FIG. 1, an outer surface (lower surface) of the plurality of ceilings (111), an inner surface of the portion of the fourth side wall (6), the first side wall (3), the portion of the second side wall (4), the first partition E, an entrance room (7) enclosed by the plurality of honeycomb floors (22), an wind shower room (8) and a circulation room (9) so as to form by arranging along the first side wall (3) from the first adjacent connecting side D to the first adjacent connecting side A, wherein, the entrance room (7) has a washbasin (71) and a plurality of exhaust-connected pipes (15). One end of the exhaust-connected pipe (15) has an inlet end penetrating through the ceiling (111) while the other end of the exhaust-connected pipes (15) is an outlet end (in other embodiment, the outlet end is connected to the fresh-air pipe (113)) making the pathogenic air in the bedroom (10) flow into the semi-hermetic space (24) through the honeycomb floor (22) and then circulate to the air filtration unit (FFU) (114) to be filtered. In this way, the cleanliness of the air in the bedroom (10) will be improved. In another embodiment as shown in FIG. 1, FIG. 2, and FIG. 3, the entrance room (7), the wind shower chamber (8) and the circulation chamber (9) are not necessary to provide but to have the inlet end of exhaust-connected pipe (15) communicate directly to the semi-hermetic space (24) below the honeycomb floors (22) making the pathogenic air in the bedroom (10) flow into semi-hermetic space (24) via the honeycomb floor (22) and further circulate to the air filtration unit (FFU) (114) to be filtered.

The bedroom (10) is combined by the space under the air filtration unit (FFU) (114), a plurality of ceilings (111), part of the second side wall (4), part of the fourth side wall (6), the first partition (E), a second partition board (F) and the plurality of honeycomb floors (22). The bedroom (10) has a single bed (101). Moreover, both the bedroom (10) and the entrance room (7), the wind shower room 8 and the circulation room 9 are separated from each other by the first partition board (E). Moreover, as shown in FIG. 1, there is a communication mouth (E1) communicates between the bedroom (10) and the circulation room (9), wherein the communication mouth (E1) has a bedroom door (E11) furnished. As shown again in FIG. 1, the bedroom (10) has a plurality of bedroom honeycomb floors (221) while the circulation room (9) has a plurality of circulating room honeycomb floor (222). The aforementioned plurality of honeycomb floors (22) is a combination of the plurality of bedroom honeycomb floors (221) and the plurality of circulating room honeycomb floors (222).

Figure 8:
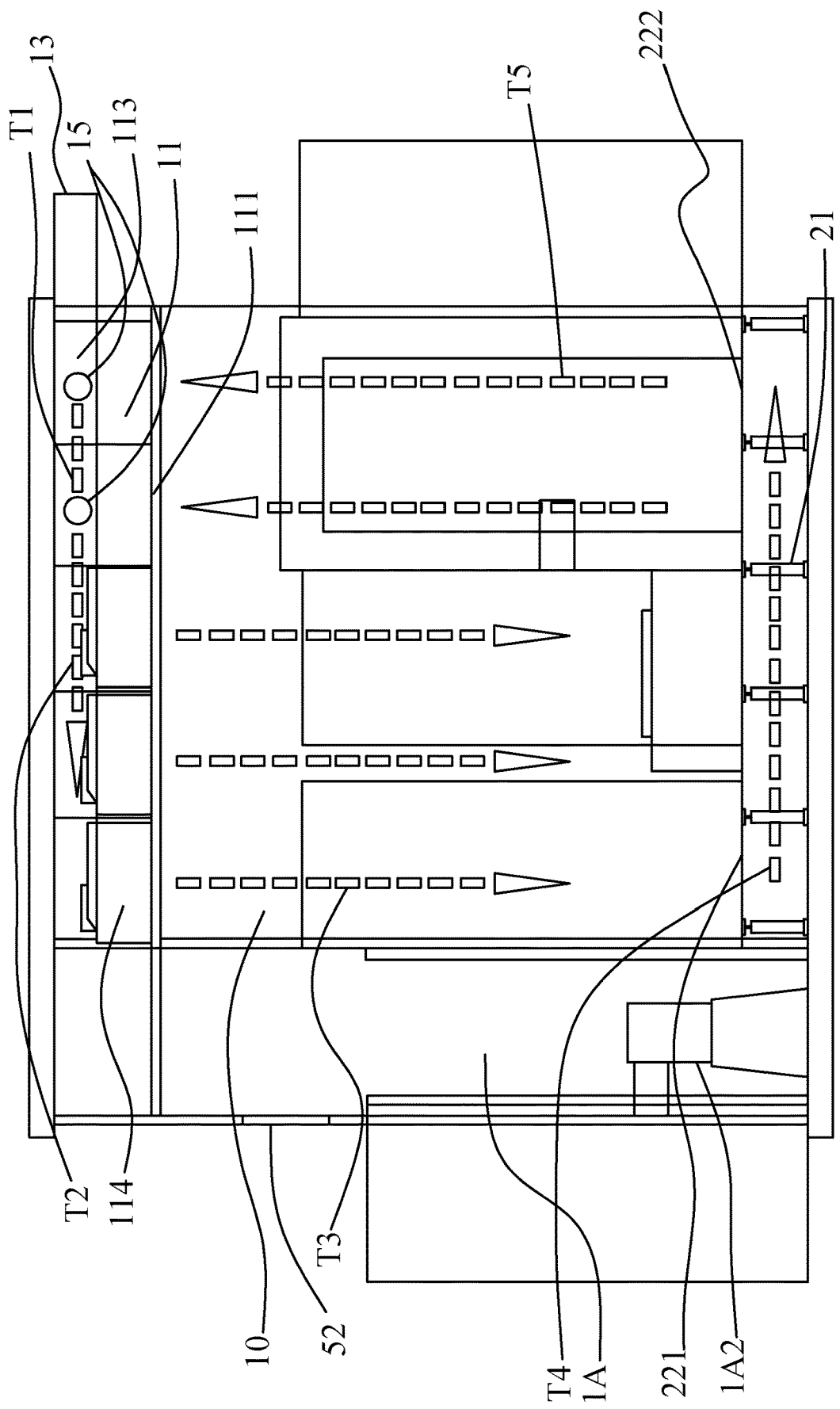
FIG. 8 is a diagram of the air circulation path of the preferred embodiment of the improved isolation ward structure of the invention.

As far as this embodiment is concerned, as shown in FIG. 2, the first partition board (E) is a storage board with an inclined honeycomb trough. The ceiling (111) under the clearance room (12), the fourth side wall (6), the third side wall (5), the second side wall (4), the second partition board F and the floor (23) form a bathroom (1A), wherein the bathroom (1A) and the bedroom (10) are separated from each other by a second partition board F. As shown in FIG. 1 and FIG. 8, there is a second communication opening (F1) between the bathroom (1A) and the bedroom (10). Moreover, the second communication opening (F1) is furnished with a bathroom door (F11) while the bathroom (1A) possess a washbasin (1A1), a flush toilet (1A2) and other sanitary facilities (not shown in the figure); In this embodiment, the second partition board (F) is a storage board with inclined honeycomb troughs.

FIG. 8 is a diagram of the air circulation path of the preferred embodiment of the improved isolation ward structure of the invention. As shown in FIG. 8, a path (T1) of the air is the path of the fresh air that enters through both of the wind pipe (13) and the fresh-air pipe (113). As shown in FIG. 2 and FIG. 3, the air that flows through the communication pipe (14) and enters the air filtration unit (FFU) (114) is the air needed to be filtered. The path (T2) is the path of this air in path (T1). The air, flowing through the plurality of exhaust-connected pipe (15) and the plurality of communication pipe (14), that is needed to be filtered, together with the fresh air in path (T1) will all enter into the air filtration unit (FFU) (114) to enhance filtering effect. The air that is filtered out through the air filtration unit (FFU) (114) and enters into the bedroom (10) forms a path (T3). After the air flowing through the bedroom (10), the virus-polluted air generated by the patients will pass through the plurality of bedroom honeycomb floors (221) and enter the semi-hermetic space (24) at the bottom portion (2) that is supported by the plurality of floor support structures (21) to form a path (T4). The virus-polluted air in the semi-hermetic space (24) at the bottom portion (2) will again flow through the circulating room honeycomb floor (222), most of the air enter the circulation room (9) and wind shower room (8), a small amount of the air pass through the entrance room (7) to form a path (T5). The virus-polluted air in the semi-hermetic space (24) at the bottom portion (2) will again flow through the plurality of exhaust-connected pipes (15) and enter into the fresh-air pipe (113), and if the bath room door (F11) opens, part of the air will flow through the a exhaust device (52) of the bathroom (1A) and the bathroom door (F11) to discharge out, further to have a substituted fresh air to enter. In this way of cycle over and over, the air needed to be filtered mixes with the fresh air and again passes through the procedure of filtration, and further recycle through the other path without passing through the patient's room, and to discharge the air at any time to substitute the fresh air to enter back, thereby, to keep the isolation ward with fresh air.

Figure 9:
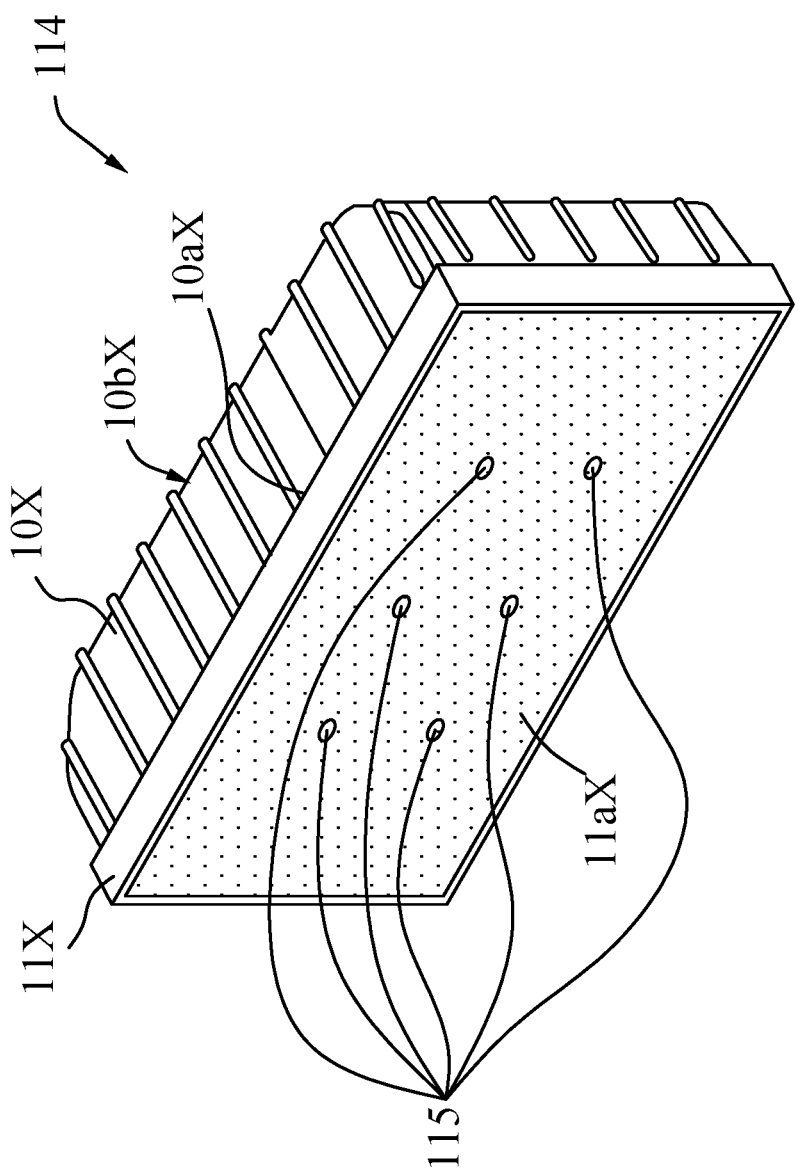
FIG. 9 is an isometric view of an air filtration unit of the preferred embodiment of the improved isolation ward structure of the invention.

FIG. 9 is an isometric view of an air filtration unit (114) of the preferred embodiment of the improved isolation ward structure of the invention. The air filtration unit (114) have acquired "NEW MODEL" Patent—Republic of China with Certificate No. M594110. As shown in FIG. 9, the air filtration unit (FFU) (114) includes a housing (10X), a filter assembly (11X), and an action assembly (not shown in the figure), wherein the filter assembly (11X) has a filter mesh structure (11aX). The housing (10X) being in the shape of a trough and integrally formed has a first side (10aX) and a second side (10bX) wherein the first side (10aX) is greater than the second side (10bX) and the first side (10aX) serves as an air outlet port of the air flow while the second side (10bX) serves as an air inlet port in order to enhance the air flow efficiency, i.e. to enhance the filtration efficiency. A pair of ribs are furnished to strengthen the stiffness of the structure as well as to lower the vibration and noise created.

In the improved isolation ward structure of the present invention, heating-added sterilization devices (115) can be furnished at the communication pipe (14) (FIG. 1), the exhaust-connected pipe (15) (FIG. 1), filter-mesh structure (11aX) (FIG. 9) and the semi-hermetic space (24). In this embodiment, the heating-added sterilization devices (115) are devices furnished with ultraviolet light or UVC-LED irradiated photo-catalyst TiO2/Ag2. In this way, the goal of double purification, i.e. dust removal and virus disposal and clean indoor air.

To summarize the above-described statement, the improved isolation ward structure of the invention possesses the following advantages which the prior arts don't have:

1. The newly created elevated floor forms a semi-hermetic space to eliminate the pathogenic air in the bedroom of the patient. Moreover, the floor is a honeycomb floor, so that the pathogenic air of the patient can flow into the semi-hermetic space, and the pathogenic air can flow into another path to be filtered.

2. It has a filtering system, and the new air and the air to be filtered can be mixed to enter the air filtering system to dilute the virus content in the air to be filtered. Therefore, the present invention is a technology that has never been seen before that resolve the problems that cannot be resolved in the prior art.

It will become apparent to those people skilled in the art that various modifications and variations can be made to the structure of the invention without departing from the scope or spirit of the invention. In view of the foregoing description, it is intended that all the modifications and variation fall within the scope of the following appended claims and their equivalents.

What is claimed is:

1. An improved isolation ward structure comprising:
   a top portion further comprising a space, a fresh-air pipe, a communication pipe and an exhaust-connected pipe wherein the space is furnished with an air filtration unit (FFU); an end of the communication pipe is communicated with the fresh-air pipe while other end of the communication pipe is communicated with the air filtration unit (FFU), an end of the exhaust-connected pipe is communicated with the fresh-air pipe;
   a bedroom being positioned under the air filtration unit (FFU) will let an air which is filtered through the air filtration unit (FFU) enter the bedroom;
   a bottom portion being positioned under the bedroom has a semi-hermetic space formed by a plurality of elevated honeycomb floors; the air within the bedroom will enter the semi-hermetic space which will let a pathogenic air within the bedroom flow therein via the plurality of honeycomb floors and re-circulate through the air filtration unit (FFU) to be filtered; and
   a backflow circulation portion being positioned above the semi-hermetic space and below the space with its upper end communicating communicates with the other end of the exhaust-connected pipe; the backflow circulation portion is adjacent to the bedroom for re-circulating the air waited to be filtered within the semi-hermetic space to the fresh-air pipe therein.

2. The improved isolation ward structure as claimed in claim 1 wherein the plurality of ceilings and plurality of supporting structures are furnished below the space; the plurality of ceilings being supported by the plurality of supporting structures have the air filtration unit (FFU) furnished thereon; the fresh-air pipe is communicated with the air filtration unit (FFU).

3. The improved isolation ward structure as claimed in claim 1 wherein the semi-hermetic space further comprising a floor, a plurality of floor support structures, and the plurality of honeycomb floors in which the plurality of honeycomb floors are installed on the plurality of floor support structures to make the plurality of honeycomb floors become an elevated floors above the floor.

4. The improved isolation ward structure as claimed in claim 3 wherein the floor support structure further comprising a securing seat, a supporting tube, a supporting seat, a tube cover, a top base, a plurality of holes and a screw bolt, wherein the securing seat and the supporting tube are combined together in which the supporting tube is a hollow body, and the tube cover being furnished at its upper end has internal threads; the supporting seat is a T-shaped structure with a top base at its upper end that can be secured to the honeycomb floors through a number of holes by employing screws and nuts while the lower end of the holes is a screw bolt so that the supporting seat can be connected by screwing with the cap on the support tube and can be used to adjust the height of the honeycomb floors.

5. The improved isolation ward structure as claimed in claim 1 further comprising:
   a first side wall being connected to the top portion and the bottom portion respectively further comprising an inlet and a fresh air mouth; the fresh air will flow through the fresh air mouth and enter the space;
   a second side wall connected to the top portion and the bottom portion respectively; a first adjacent connecting side is formed by connecting the first side wall and the second side wall;
   a third side wall being connected to the top portion and the bottom portion respectively further comprising an outlet and an exhaust device; a second adjacent connecting side is formed by the second side wall and the third side wall;
   a fourth side wall connected to the top portion and the bottom portion respectively; a third adjacent connecting side is formed by the third side wall and the fourth side wall while a fourth adjacent connecting side is formed by the fourth side wall and the first side wall; in this way, a hexagon is then formed.

6. The improved isolation ward structure as claimed in claim 5 wherein All of the first side wall, the second side wall, the third side wall and the fourth side wall are made of cement or brick and then coated with epoxy after curing.

7. The improved isolation ward structure as claimed in claim 5 wherein the plurality of ceilings, the fourth side wall, the first side wall, the second side wall and the external surface of the plurality of honeycomb floors further encloses to form a wind shower room such that the entrance room, the wind shower room and the circulation room are arranged to form from the fourth adjacent connecting side toward the first adjacent connecting side along the first side wall.

8. The improved isolation ward structure as claimed in claim 1 wherein the backflow circulation portion being formed by enclosing the plurality of ceilings, the fourth side wall, the first side wall, the second side wall and the plurality of honeycomb floors, further comprising an entrance room, a circulation room snd the fourth adjacent connecting side.

9. The improved isolation ward structure as claimed in claim 1 further comprising portion below the air filtration unit (FFU), the plurality of ceilings, a portion of the second side wall, a portion of the fourth side wall, a first partition board, a second partition board, as well as the plurality of honeycomb floors.

10. The improved isolation ward structure as claimed in claim 1 further comprising a bathroom which is formed by being enclosed by the fourth side wall, the third side wall, the second side wall, the plurality of ceilings and the floor; the bathroom and the bedroom are separated each other by the a second partition board (F); the bathroom is communicated with the bedroom by having a second communication opening furnished between them.

11. The improved isolation ward structure as claimed in claim 1 wherein the plurality of honeycomb floors possesses perforations to facilitate the air to pass through.

12. The improved isolation ward structure as claimed in claim 1 further comprising a heating-added sterilization device which being devices furnished with ultraviolet light or UVC-LED irradiated photo-catalyst TiO2/Ag2 can be furnished at the communication pipe, the exhaust-connected pipe or the semi-hermetic space.

13. An improved isolation ward structure comprising:
a top portion further comprising a space, a fresh-air pipe, and a communication pipe wherein the top portion is furnished with an air filtration unit (FFU); an end of the communication pipe is communicated with the fresh-air pipe while other end of the communication pipe is communicated with the air filtration unit (FFU);
a bedroom being positioned under the air filtration unit (FFU) will let the air filtered through the air filtration unit (FFU) to enter therein;
a bottom portion being positioned under the bedroom has a semi-hermetic space formed by the plurality of elevated honeycomb floors; the air within the bedroom will enter the semi-hermetic space which will let a pathogenic air within the bedroom flow therein via a plurality of honeycomb floors and re-circulate through the air filtration unit (FFU) to be filtered; and
an exhaust-connected pipe with an entrance end of which is communicated with the semi-hermetic space which is positioned below the plurality of honeycomb floors while the other end is communicated with the fresh-air pipe making the pathogenic air within the bedroom (10) flow into the semi-hermetic space through the plurality of honeycomb floors and re-circulate to the air filtration unit (FFU) to be filtered.

14. The improved isolation ward structure as claimed in claim 13 wherein a plurality of ceilings and a plurality of air filtration unit (FFU) are furnished in the middle or lower portion of the space wherein the air filtration unit (FFU) is furnished on the plurality of ceilings, and the plurality of ceilings are supported by the plurality of supporting structures; the fresh-air pipe is communicated with the air filtration unit (FFU).

15. The improved isolation ward structure as claimed in claim 13 wherein the semi-hermetic space further comprising the floor, the plurality of floor support structures, and the plurality of honeycomb floors in which the plurality of honeycomb floors are installed on the plurality of floor support structures to make the plurality of honeycomb floors become an elevated floors above the floor.

16. The improved isolation ward structure as claimed in claim 15 wherein the floor support structure further comprising a securing seat, a supporting tube, a supporting seat, a tube cover, a top base, a plurality of holes and a screw bolt, wherein the securing seat and the supporting tube are combined together in which the supporting tube is a hollow body, and the tube cover being furnished at its upper end has internal threads; the supporting seat is a T-shaped structure with a top base at its upper end that can be secured to the honeycomb floors through a number of holes by employing screws and nuts while the lower end of the holes is a screw bolt so that the supporting seat can be connected by screwing with the cap on the support tube and can be used to adjust the height of the honeycomb floors.

17. The improved isolation ward structure as claimed in claim 13 further comprising:
a first side wall being connected to the top portion and the bottom portion respectively further comprising an inlet and a fresh air mouth; the fresh air will enter the fresh-air pipe (113) through the fresh air mouth;
a second side wall connected to the top portion and the bottom portion respectively; a first adjacent connecting side is formed by the first side wall and the second side wall;
a third side wall being connected to the top portion and the bottom portion respectively further comprising an outlet and an exhaust device; a second adjacent connecting side is formed by the second side wall and the third side wall;
a fourth side wall connected to the top portion and the bottom portion respectively; a third adjacent connecting side is formed by the third side wall and the fourth side wall while a fourth adjacent connecting side is formed by the fourth side wall and the first side wall; in this way, a hexagon is then formed.

18. The improved isolation ward structure as claimed in claim 13 further comprising portion below the air filtration unit (FFU), the plurality of ceilings, a portion of the second side wall, a portion of the fourth side wall, a first partition board, a second partition board, as well as the plurality of honeycomb floors.

19. The improved isolation ward structure as claimed in claim 13 further comprising a bathroom which is formed by being enclosed by the fourth side wall, the third side wall, the second side wall, the plurality of ceilings and the floor; the bathroom and the bedroom are separated each other by the a second partition board; the bathroom is communicated with the bedroom by having a second communication opening furnished between them.

20. The improved isolation ward structure as claimed in claim 13 wherein the plurality of honeycomb floors possesses perforations to facilitate the air to pass through.

21. The improved isolation ward structure as claimed in claim 13 further comprising a heating-added sterilization device which being devices furnished with ultraviolet light or UVC-LED irradiated photo-catalyst TiO2/Ag2 can be furnished at the communication pipe, the exhaust-connected pipe or the semi-hermetic space.

* * * * *